US011893623B1

(12) United States Patent
Bhow (10) Patent No.: US 11,893,623 B1
(45) Date of Patent: Feb. 6, 2024

(54) SYSTEM FOR DISPLAYING DYNAMIC PHARMACY INFORMATION ON A GRAPHICAL USER INTERFACE

(71) Applicant: WALGREEN CO., Deerfield, IL (US)

(72) Inventor: Gunjan Dhanesh Bhow, Menlo Park, CA (US)

(73) Assignee: WALGREEN CO., Deerfield, IL (US)

( * ) Notice: Subject to any disclaimer, the term of this patent is extended or adjusted under 35 U.S.C. 154(b) by 533 days.

(21) Appl. No.: 16/888,503

(22) Filed: May 29, 2020

(51) Int. Cl.
   *G06Q 30/00* (2023.01)
   *G06Q 30/0601* (2023.01)
   *G16H 20/10* (2018.01)
   *G06N 20/00* (2019.01)

(52) U.S. Cl.
   CPC ......... *G06Q 30/0639* (2013.01); *G06N 20/00* (2019.01); *G06Q 30/0643* (2013.01); *G16H 20/10* (2018.01)

(58) Field of Classification Search
   CPC ........... G06Q 30/0639; G06Q 30/0643; G16H 20/10; G06N 20/00
   See application file for complete search history.

(56) References Cited

U.S. PATENT DOCUMENTS

| | | | |
|---|---|---|---|
| 7,302,429 B1 * | 11/2007 | Wanker | G06Q 30/0627 707/999.005 |
| 7,953,873 B1 | 5/2011 | Madurzak | |
| 9,282,161 B1 | 3/2016 | Hill | |
| 11,188,970 B1 | 11/2021 | Xu | |
| 2002/0035515 A1 * | 3/2002 | Moreno | B65G 1/0485 340/5.73 |
| 2007/0294129 A1 | 12/2007 | Froseth | |

(Continued)

FOREIGN PATENT DOCUMENTS

JP    2018073066 A  *  5/2018

OTHER PUBLICATIONS

Fernando, Tasha J., Duy D. Nguyen, and Larry J. Baraff. "Effect of electronically delivered prescriptions on compliance and pharmacy wait time among emergency department patients." Academic Emergency Medicine 19.1 (2012): 102-105. (Year: 2012).*

(Continued)

*Primary Examiner* — Matthew E Zimmerman
(74) *Attorney, Agent, or Firm* — MARSHALL, GERSTEIN & BORUN LLP; Randall G. Rueth (57) ABSTRACT

The following relates generally to pharmacy and/or merchandise pickup location selection. In some embodiments, factors are used to determine a pharmacy and/or merchandise pickup location selection for an individual. In this regard, the factors may include: whether the pharmacy and/or merchandise pickup location has a medication in stock; wait time at the pharmacy and/or merchandise pickup location; geographic distance to the individual; travel time from the location of the individual; urgency of filling a prescription; price of a prescription; whether another product or class of products available at the pharmacy and/or merchandise pickup location; and/or whether a locker is available at the pharmacy and/or merchandise pickup location. In some embodiments, Artificial Intelligence (AI) is used to create a model of pharmacy and/or merchandise pickup location selection for the individual.

23 Claims, 8 Drawing Sheets

(56) References Cited

U.S. PATENT DOCUMENTS

| | | | |
|---|---|---|---|
| 2013/0054258 A1* | 2/2013 | Cohan | G06Q 40/08 705/2 |
| 2013/0103697 A1 | 4/2013 | Hill | |
| 2013/0325494 A1* | 12/2013 | Angel | G06Q 30/0261 705/2 |
| 2014/0330603 A1 | 11/2014 | Corder | |
| 2015/0081348 A1 | 3/2015 | Avera | |
| 2015/0142479 A1* | 5/2015 | Porter | G06Q 40/08 705/4 |
| 2015/0242590 A1* | 8/2015 | Taylor | G16H 10/60 705/2 |
| 2016/0307265 A1* | 10/2016 | Seaward | G06Q 30/0631 |
| 2017/0235792 A1 | 8/2017 | Mawji | |
| 2018/0053240 A1 | 2/2018 | Jones | |
| 2018/0082361 A1 | 3/2018 | Wilkinson | |
| 2018/0292218 A1 | 10/2018 | Swain | |
| 2019/0257665 A1 | 8/2019 | Friedman | |
| 2019/0259232 A1* | 8/2019 | Nandakumar | G07F 17/10 |
| 2019/0311445 A1 | 10/2019 | Werner | |
| 2020/0020001 A1 | 1/2020 | Singh | |
| 2020/0279191 A1 | 9/2020 | Koch et al. | |
| 2021/0065862 A1 | 3/2021 | Siegel | |
| 2021/0231454 A1 | 7/2021 | Jindal | |

OTHER PUBLICATIONS

Nicholson, Alexander Marshall. Generalization error estimates and training data valuation. California Institute of Technology, 2002. (Year: 2002).*

Non-Final Office Action for U.S. Appl. No. 16/888,536, dated Jul. 27, 2022.

Non-final Office Action for U.S. Appl. No. 16/888,536, dated Aug. 17, 2023.

* cited by examiner

Suggested Pharmacies

Pharmacy 1
Time to fill prescription: 20 minutes
Wait time at pharmacy: 10 minutes
Travel time: 15 minutes
Address: xxx    Phone: xxx
Cost to fill prescription: $$$

Pharmacy 2
Time to fill prescription: 1 hour
Wait time at pharmacy: 2 minutes
Travel time: 25 minutes
Address: xxx    Phone: xxx
Cost to fill prescription: $$$

Pharmacy 3
Time to fill prescription: 45 minutes
Wait time at pharmacy: 15 minutes
Travel time: 25 minutes
Address: xxx    Phone: xxx
Cost to fill prescription: $$$

Pharmacy 4
Time to fill prescription: 35 minutes
Wait time at pharmacy: 0 minutes
Travel time: 45 minutes
Address: xxx    Phone: xxx
Cost to fill prescription: $$$

SYSTEM FOR DISPLAYING DYNAMIC PHARMACY INFORMATION ON A GRAPHICAL USER INTERFACE

BACKGROUND

Often, to fill a prescription, a medical patient (e.g., an individual) may have to decide between pharmacies. However, the individual may not have enough information to make the decision best suited to the individual's needs, or may encounter other difficulties in deciding between pharmacies. This may result in, for example, the individual selecting a pharmacy that is not the best suited to the individual's needs.

In addition, when purchasing a merchandise item that requires preparation time, such as a meal kit or beauty box, a customer may have difficulty selecting between locations to pickup the merchandise item at.

The systems and methods disclosed herein provide solutions to these problems and others.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one aspect, there is a computer system for selecting a pharmacy. The computer system may include one or more processors configured to: using a machine learning algorithm and an initial training dataset, build a pharmacy selection model of an individual, wherein the initial data training dataset comprises data regarding: (i) which pharmacy or pharmacies the individual has previously used; (ii) travel times to the previously used pharmacies; (iii) wait times at previously used pharmacies; (iv) prices of medications the individual has purchased at the previously used pharmacies; (v) whether another product or class of products was available at the previously used pharmacies; and/or (vi) whether a locker was available at the previously used pharmacies; receive: (i) an electronic indication of a medication for the individual, and (ii) a location of the individual; and determine one or more pharmacies to be presented to the individual, the one or more pharmacies determined based on: (i) the pharmacy selection model of the individual, (ii) the electronic indication of the medication, and (iii) the location of the individual In another aspect, there is another computer system for selecting a pharmacy, the computer system comprising one or more processors configured to: receive an indication of a medication; determine a location of an individual; identify a plurality of pharmacies based on a first factor; and select a preferred pharmacy from the plurality of pharmacies based on a second factor.

In yet another aspect, there is another computer system for selecting a pharmacy, the computer system comprising one or more processors configured to: receive an indication of a medication; determine a location of an individual; identify a plurality of pharmacies; determine: (i) a travel time from the location of the individual to each pharmacy of the plurality of pharmacies, and (ii) for each pharmacy of the plurality of pharmacies, a prescription fill time; and select a preferred pharmacy from the plurality of pharmacies based on: (i) the determined travel time, and (ii) the determined prescription fill times.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

Figure 1:
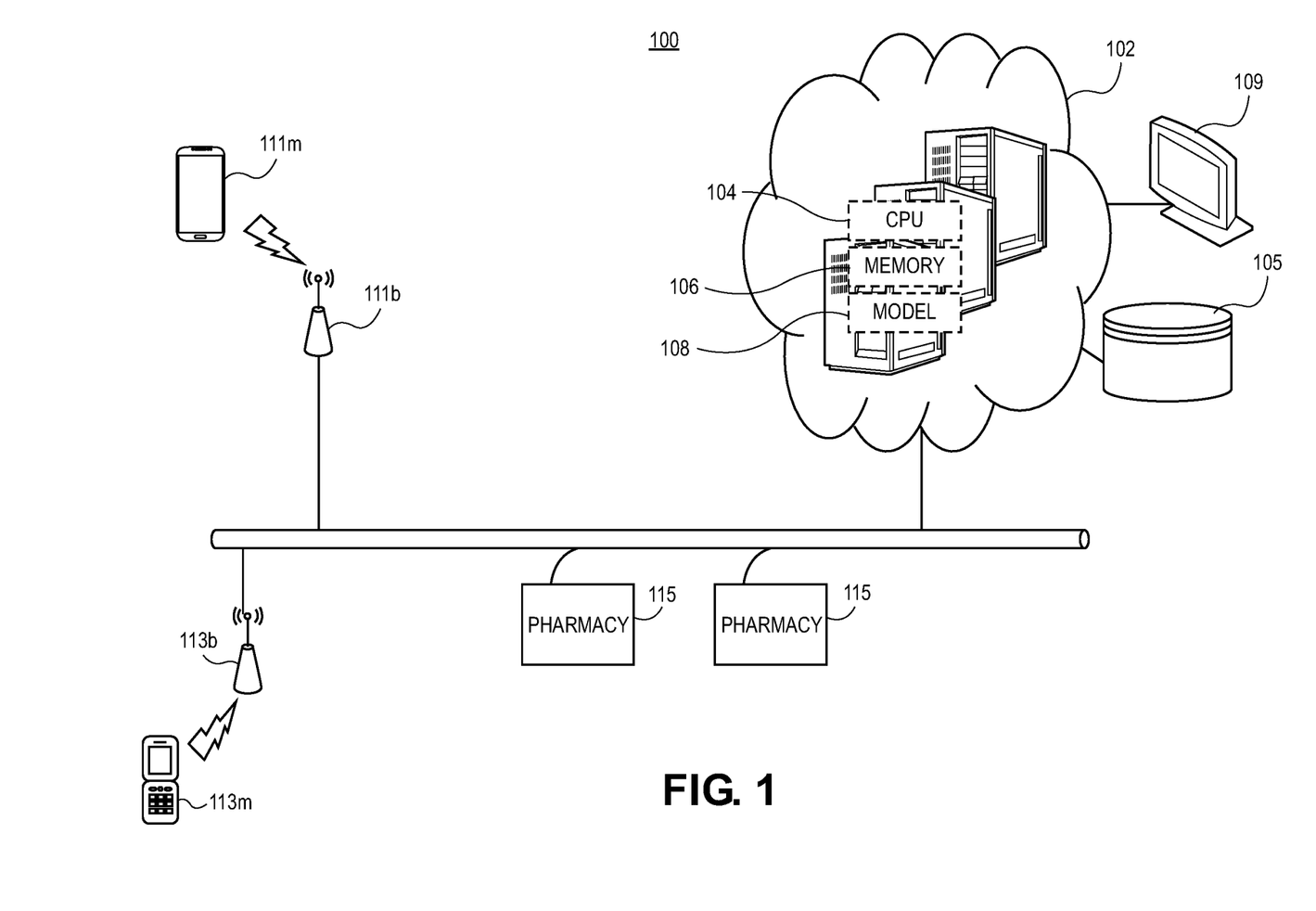
FIG. 1 illustrates an example infrastructure for selecting a pharmacy and/or merchandise pickup location.

The present embodiments relate to, inter alia, to pharmacy selection and/or merchandise pickup location selection.
Exemplary Infrastructure FIG. 1 illustrates a platform 100 configured to select a pharmacy and/or merchandise pickup location in accordance with various embodiments disclosed herein. In the example embodiment of FIG. 1, the platform 100 includes server(s) 102, which may comprise one or more computer servers. In various embodiments, server(s) 102 comprise multiple servers, which may comprise multiple, redundant, or replicated servers as part of a server farm. In still further embodiments, server(s) 102 are implemented as cloud-based servers. For example, server(s) 102 may comprise a cloud-based platform such as MICROSOFT AZURE, AMAZON AWS, or the like.

Server(s) 102 may include one or more processor(s) 104 as well as one or more computer memories 106. The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memories 106 may store an operating system (OS) (e.g., Microsoft Windows, Linux, Unix, etc.) capable of facilitating the functionalities, apps, methods, or other software as discussed herein. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, the machine learning component and/or the provisioning application, where each are configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 105 (e.g., a relational database, such as Oracle, DB2, MySQL, or a NoSQL based database, such as MongoDB). The data stored in the memories 106 and/or the database 105 may include all or part of any of the data or information described herein, including, for example, the one or more search requests, the one or more transaction details, and the profile information of the user.

The server(s) 102 may further include a communication component configured to communicate (e.g., send and receive) data via one or more external/network port(s) to one or more networks or local terminals, such as computer network 120 and/or terminal 109 (for rendering or visualizing) as described herein. In some embodiments, server(s) 102 may include a client-server platform technology such as ASP.NET, Java J2EE, Ruby on Rails, Node.js, a web service or online API, responsive for receiving and responding to electronic requests. The server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120.

Server(s) 102 may further include or implement an operator interface configured to present information to an administrator or operator and/or receive inputs from the administrator or operator. As shown in FIG. 1, an operator interface may provide a display screen (e.g., via terminal 109). Server(s) 102 may also provide I/O components (e.g., ports, capacitive or resistive touch sensitive input panels, keys, buttons, lights, LEDs), which may be directly accessible via or attached to server(s) 102 or may be indirectly accessible via or attached to terminal 109. According to some embodiments, an administrator or operator may access the server(s) 102 via terminal 109 to review information, make changes, input training data, and/or perform other functions.

As described above herein, in some embodiments, server(s) 102 may perform the functionalities as discussed herein as part of a "cloud" network or may otherwise communicate with other hardware or software components within the cloud to send, retrieve, or otherwise analyze data or information described herein. Furthermore, server(s) 102 and/or their respective memorie(s) 106 are configured to store data including for example, patient data, pharmacy data, prescription data, and so forth.

In general, a computer program or computer based product, or application, (e.g., the medical adherence application (app)) in accordance with some embodiments may include a computer usable storage medium, or tangible, non-transitory computer-readable medium (e.g., standard random access memory (RAM), an optical disc, a universal serial bus (USB) drive, or the like) having computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C #, Objective-C, Java, Scala, Actionscript, Javascript, HTML, CSS, XML, etc.).

In the example embodiment of FIG. 1, server(s) 102 are communicatively connected, via computer network 120 and base stations 111*b* and 113*b* to respective mobile devices 111*m* and 113*m*. Computer network 120 may comprise a packet based network operable to transmit computer data packets among the various devices and servers described herein. For example, computer network 120 may consist of any one or more of Ethernet based network, a private network, a local area network (LAN), and/or a wide area network (WAN), such as the Internet. In addition, in some embodiments, computer network 120 may comprise cellular or mobile networks to facilitate data packet traffic (e.g., mobile device movement data) to and from base stations 111*b* and/or 113*b*. Base stations 111*b* and 113*b* may comprise cellular towers or access points implementing any one or more cellular or mobile device standards, including, for example, any of GSM, UMTS, CDMA, NMT, LTE, 5G NR, or the like.

Further in the example of embodiment of FIG. 1, pharmacies/merchandise pickup locations 115 are connected to computer network 120. As is understood in the art, the pharmacies/merchandise pickup locations 115 carry an inventory of prescription medication. The pharmacies/merchandise pickup locations 115 may communicate data of their inventory to the server(s) 102 through the computer network 120 or by any other means.

Exemplary Embodiments

The following discussion teaches systems and methods for, inter alia, pharmacy selection. For example, the following discussion teaches how to leverage the example infrastructure of FIG. 1 to select a pharmacy. And FIG. 2 shows a flowchart of an example implementation.

One objective of the systems and methods disclosed herein is to provide an individual with an optimal selection of a pharmacy to fill a prescription. Initially, the system may receive the prescription or an indication of the desired medication (e.g., at step 205 of FIG. 2). In selecting a pharmacy, a number of factors may be considered. For example, some factors that some embodiments consider are:

Whether the pharmacy has the medication in stock;
Fill time of the prescription at the pharmacy;
Wait time at the pharmacy;
Geographic distance to the individual;
Travel time to the pharmacy including traffic and other travel factors;
Urgency of filling the prescription;
Price of the prescription including if the pharmacy accepts a particular insurance provider, and alternative (e.g., generic) medications available including side effects or possible side effects of the alternative medications;
Whether another product or class of products is available at the pharmacy; and
Whether a locker is available at the pharmacy.

Figure 2:
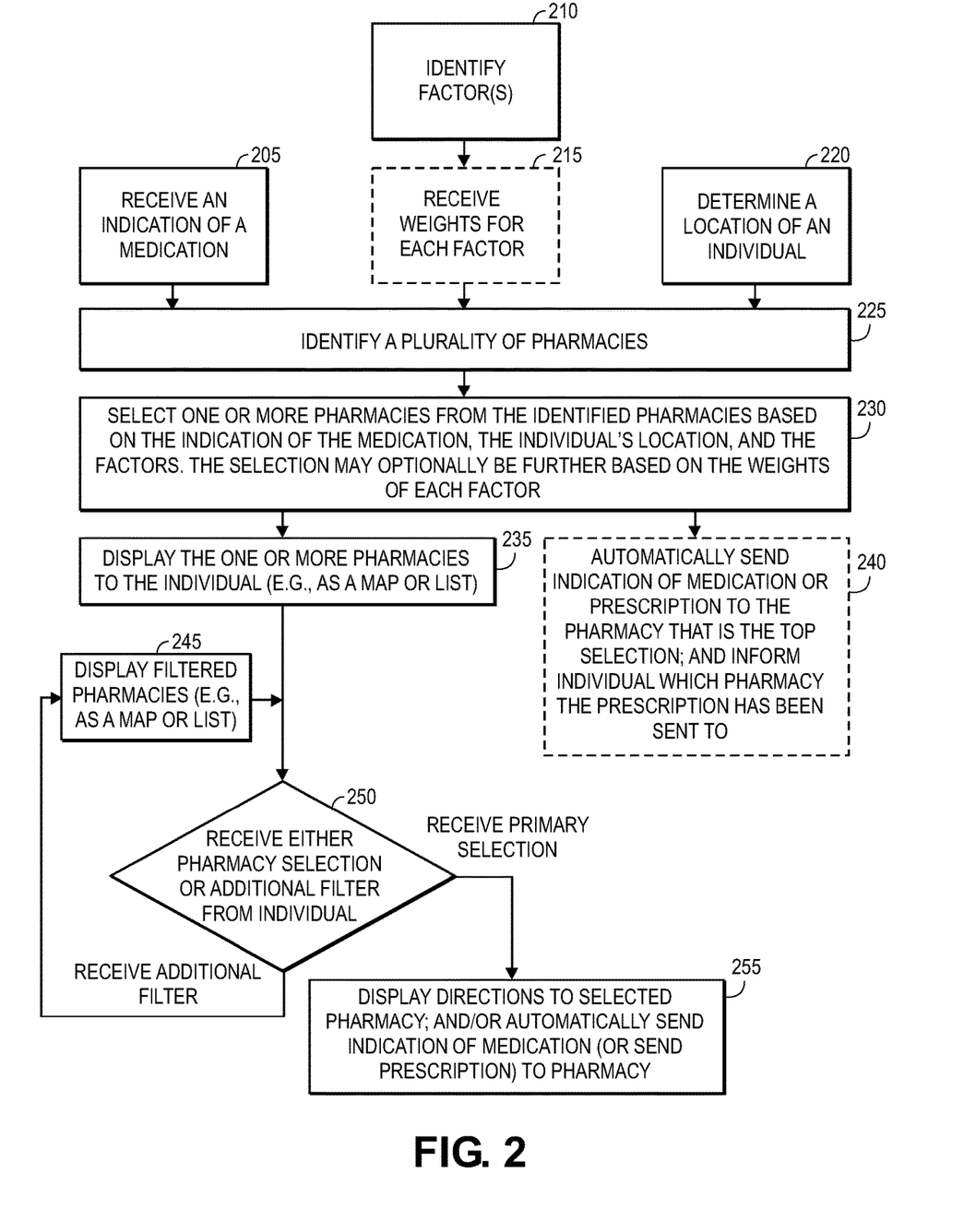
FIG. 2 shows a flowchart of an example implementation of methods described herein.

In this regard, the user/individual may identify which factors the system should consider (see, e.g., step 210 of FIG. 2). Furthermore, the user may assign weights (e.g., indications of importance) to any or all of the factors to indicate their importance (see, e.g., optional step 215 of FIG. 2). For instance, if the individual is experiencing pain that could be alleviated with the prescription, the user may assign a higher weight to an urgency factor and a lower weight to travel time to the pharmacy (e.g., the individual is willing to travel farther due to the pain the individual is experiencing). In another example, an individual might chose to wait longer for a medication in order to reduce the price; in this example, the individual might chose to allocate a higher weight to price and a lower weight to urgency.

In some embodiments, the system selects a pharmacy that has a least total time for the individual to receive the prescription; in some implementations, this is based on the prescription fill time, wait time, and travel time (e.g., using these factors, the system finds the lowest overall time that a patient/individual can receive a prescription in).

In some embodiments, the individual may specify the urgency factor as a time period that it necessary to receive the medication in (e.g., need medication within 1 hour/1 week etc.). In other embodiments, the individual may specify the urgency factor as a numerical value (e.g., as a scale from 1 to 10 with 10 being the most urgent).

In some aspects, one of the factors may be whether another product or class of products is available at the pharmacy. This allows, for example, a class of products (e.g., groceries, beauty products, healthcare products, photography products, and so forth) to be specified by the individual. This may be useful, for example, if the individual would like to do grocery shopping in addition to picking up the prescription. In another example, the individual may specify a particular product (e.g., eggs, yogurt, razor blades, deodorant, and so forth). This function is useful if the user desires to buy only a few items in addition to picking up the prescription.

Regarding the wait time at the pharmacy, any technique may be used to calculate this and some embodiments estimate this based on data received from the pharmacy. For example, camera data may be received from the pharmacy, and used to calculate the wait time. Additionally or alternately, the pharmacy may make a calculation of an estimated wait time and send it to the system.

In some implementations, the system identifies a number of pharmacies (e.g., based on one or more the above-mentioned factors) (see, e.g., step 225 of FIG. 2); and, then, select a preferred pharmacy from the identified pharmacy (e.g., again based on one or more of the above-mentioned factors) (see, e.g., step 230 of FIG. 2). For example, the system may start by identifying a plurality of pharmacies based on a geographic distance to the individual (which may be calculated from, e.g., the location of the individual determined at step 220 of FIG. 2); then, the system may select a pharmacy from the identified pharmacies based on a whether the pharmacy has a prescription in stock as well as a travel time to the pharmacy including road traffic. In other implementations, the identification and selection steps may be combined into a single step. In yet other implementations, the identification and selection steps may be broken down into any number of steps; for example, the selection step may be broken down into first and second filtering steps (e.g., a first step that filters the pharmacies based on prescription availability, and a second filtering step that filters based on price of the prescription) (see, e.g., step 250, which may be repeated any number of times based on how many filters are input by the individual).

Regarding the factor of whether the pharmacy has the medication in stock, some embodiments indicate this as a binary value (e.g., either the medication is or is not in stock). In other embodiments, whether a medication is in stock is calculated as a probability that a medication will be in stock at a particular time (e.g., including that the pharmacy will run out of the medication, or that another shipment of the medication will come in, or so forth). For instance, during allergy season, the system may know that the pharmacy typically sells medication at a particular rate, and thus may calculate a probability of whether the allergy medication will still be in stock in 24 hours, 48 hours, etc.

In some embodiments, the system automatically selects a pharmacy (see, e.g., steps 240 and 255 of FIG. 2); and in some of these embodiments, the system automatically sends the prescription to the pharmacy. In other embodiments, the system displays a list of pharmacies to the user to allow the user to select from the list. The pharmacies may also be displayed on a map, as described below (see, e.g., steps 235 and 245 of FIG. 2).

Exemplary System Display—Map Format

Figure 3:
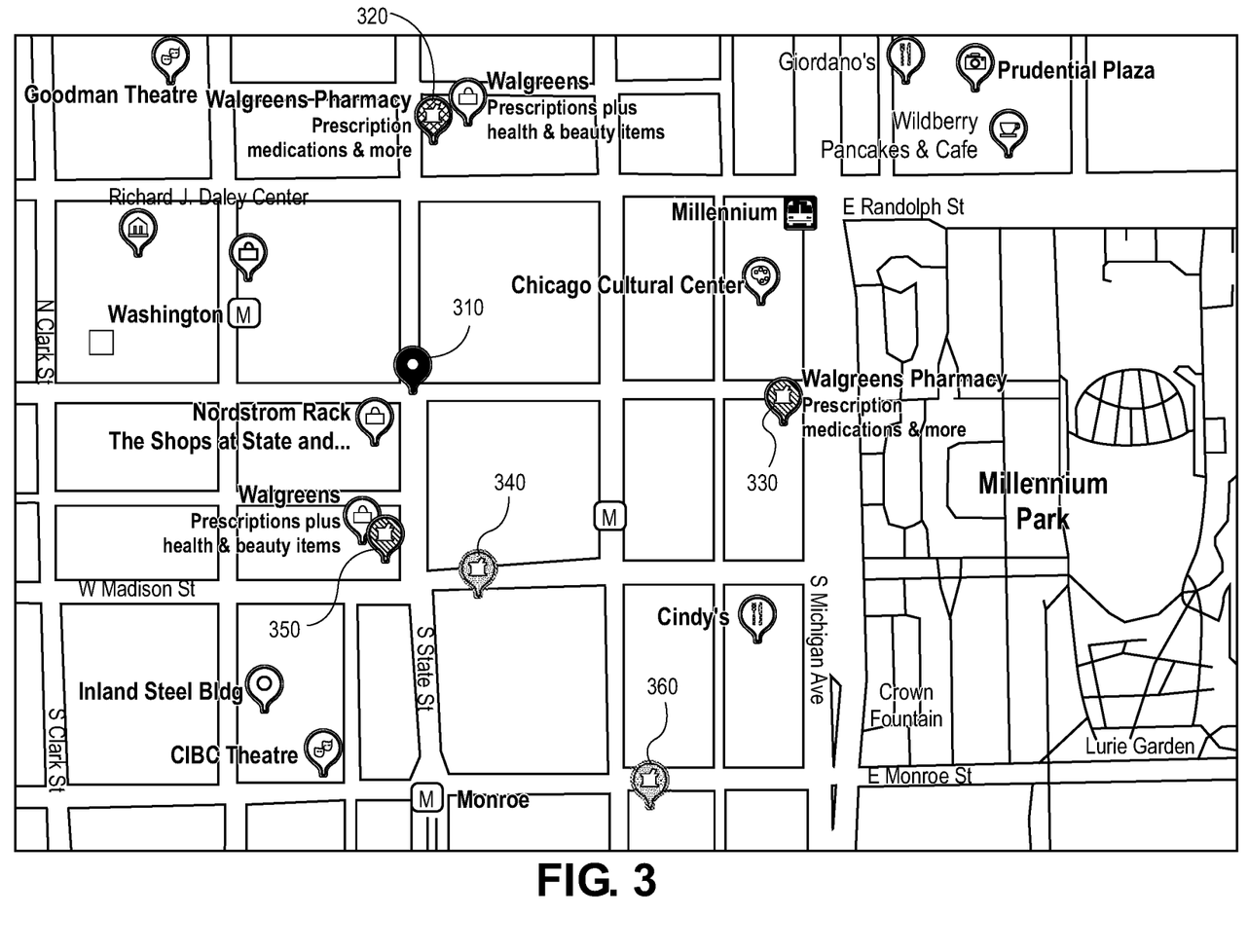
FIG. 3 illustrates an example display relating to pharmacy selection and including a map.

FIG. 3 illustrates an example display relating to pharmacy selection. With reference thereto, individual location 310 is shown along with pharmacies 320, 330, 340, 350, 360. The system may display the pharmacies in color coded form. For instance, the system may calculate a most optimal pharmacy, and display that pharmacy in green while displaying the other pharmacies in yellow or red. (For purposes of illustration, in FIG. 3, green fill for pharmacy 320 is illustrated as cross hatch, yellow fill for pharmacies 330, 350 is illustrated as hatch, and red fill for pharmacies 340, 360 is illustrated as stipple). In another example, the system may display pharmacies based on time thresholds (e.g., pharmacies with a prescription fill time below a low time threshold in green (e.g., below 1 hour); pharmacies with a prescription fill time above a high time threshold in red (e.g., 1 day); and the remainder of pharmacies in yellow). In yet another example, the pharmacies may be color coded (e.g., in green/yellow/red) according to overall scores they are each assigned based on all of the factors that the individual has specified.

In some embodiments, subsequent to viewing the map, the individual may apply a filter(s) to the displayed pharmacy. For example, the individual may further filter based on any of the factors described above (e.g., in the initial search, the urgency factor was set to providing the prescription within 2 hours, but, after seeing the results, the individual narrows the search to providing the prescription within 1 hour).

The individual location 310 may be determined any way. For example, the individual location 310 may be determined from global positioning system (GPS) data, address information input by the individual, internet protocol (IP) address information, and so forth.

Figure 4:
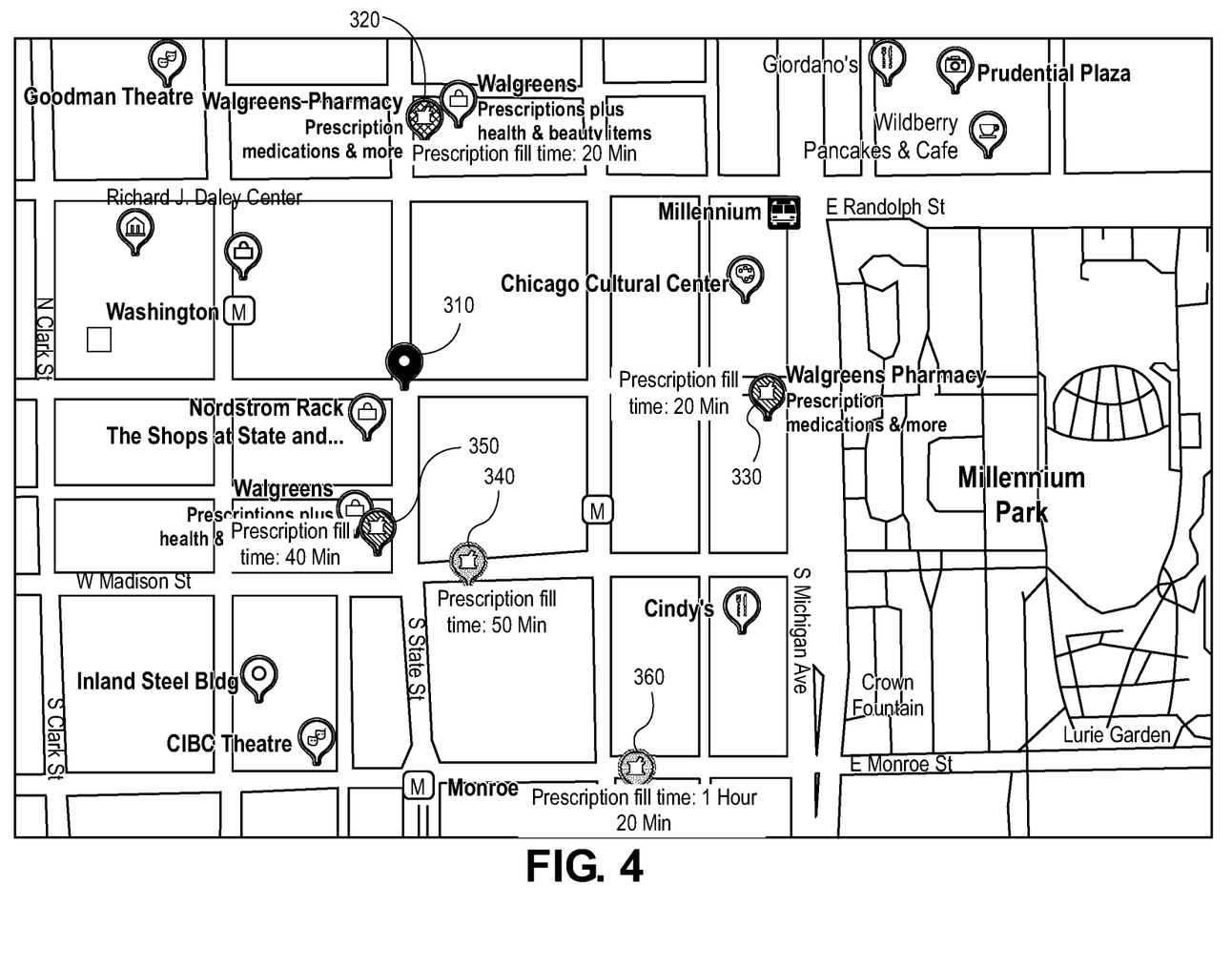
FIG. 4 illustrates an example display relating to pharmacy selection including a map with calculated prescription fill times.

In some embodiments, the system may display the calculated prescription fill times, as shown in the example of FIG. 4. For instance, FIG. 4 shows that pharmacy 320 has a prescription fill time of 20 minutes. In addition, although not shown in the example of FIG. 4, the travel time from the individual's location to the pharmacy may be shown on the map.

Exemplary System Display—List Format

Figure 5:
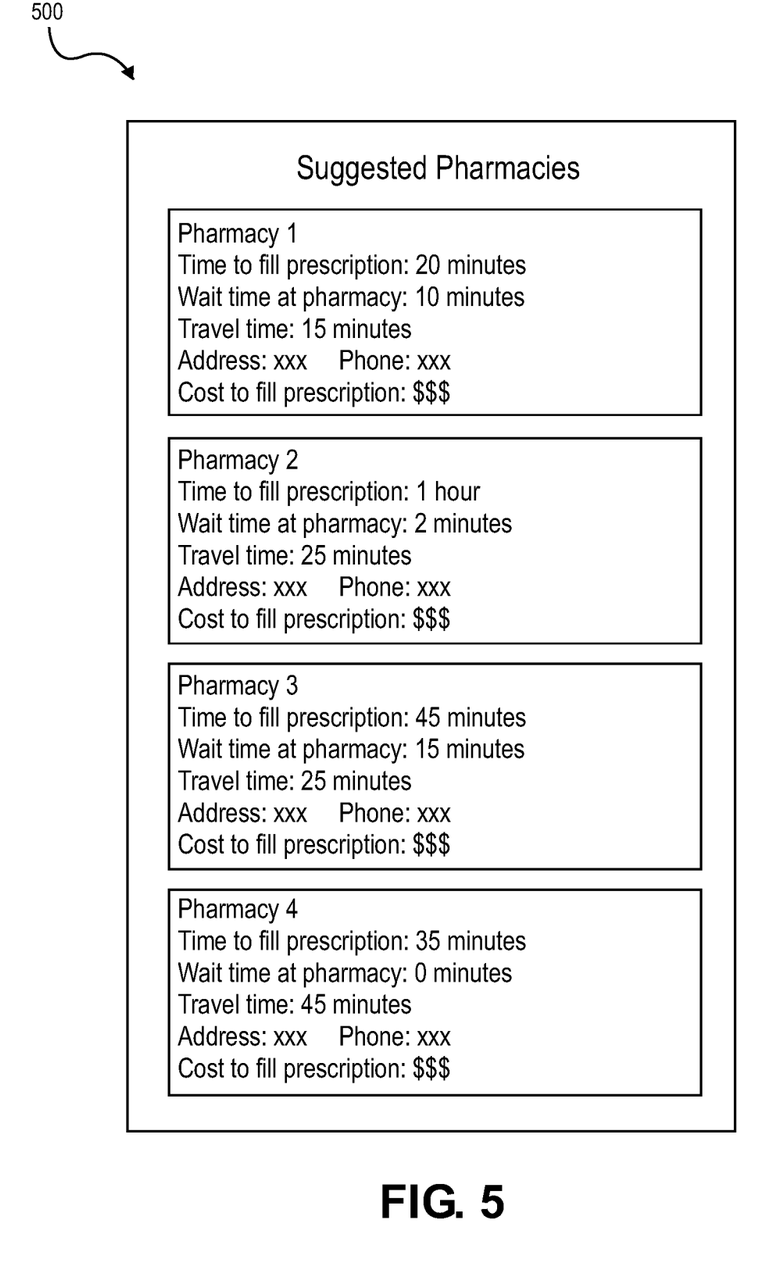
FIG. 5 illustrates an example displayed list of pharmacies.

FIG. 5 illustrates an example displayed list of pharmacies 500. In the example of FIG. 5, four pharmacies are listed along with their corresponding prescription fill time, wait time, travel time, address, phone, and cost to fill prescription. It should be understood that FIG. 5 is only one example, and that more or less information may be displayed for each pharmacy.

The list format is convenient for an individual because it allows a user to make a quick selection of a pharmacy (e.g., the individual may view the list and then select a pharmacy from the list).

In some embodiments, the individual may rank or list the pharmacies based on any of the above-mentioned factors, or any other criteria. For example, the individual may choose to rank or list the pharmacies in order of price to fill the prescription (e.g., from lowest cost to highest cost).

Lockers

Some embodiments enable the individual to pick up the prescription from a locker. For example, the individual may order the prescription from a smartphone, and then pick up the prescription along with any other ordered items from a locker.

Any means may be used to open the locker. For instance, a QR code or bar code may be sent to the individual's smart phone to allow the individual to open the locker. Alternatively or additionally, a numerical combination may be sent to the individual's smart phone, and the individual may enter the numerical combination into a keypad communicatively coupled to the locker in order to open the locker. Alternatively, or additionally, the locker may be opened by use of biometric data (e.g., fingerprint data, image data of the individual's face, data from an eye scan, and so forth).

Embodiments involving locker pickup allow for increased social distancing, which is advantageous in certain situations such as slowing the spread of a virus. Advantageously, use of lockers may also advantageously reduce an individual's wait time at the pharmacy.

Continuous Learning and Artificial Intelligence (AI)

In some implementations, AI is leveraged to improve system performance. For example any or all of the above-mentioned factors may be analyzed using AI, or used in creating an AI model. By way of brief overview, in some embodiments, there is an AI model 108 that is a model of a pharmacy selection for an individual. The AI model 108 allows for the system to accurately select a pharmacy for the individual. The AI model 108 may be continuously updated whenever the individual selects a pharmacy, or at any other point in time (e.g., when the system obtains any new information). In this regard, some embodiments create an initial AI model 108 which is then continuously updated. This continuous learning enhances the effectiveness and predictive accuracy of the AI model 108.

In various embodiments, an individual's pharmacy selection artificial intelligence model 108 is trained on a first set of data. The first set of data may include, for example, any data regarding the patient's previous selection of pharmacies. The first set of data may comprise feature training data, which may include compressed and/or transformed data, for individual's pharmacy selection artificial intelligence model 108. Training the individual's pharmacy selection artificial intelligence model 108 may include inputting a dataset (e.g., first set of data) into an AI training algorithm or platform, such as TENSORFLOW or PYTORCH. Generally, the CPU 104 stores data (e.g., in database 105 and/or memories 106), and periodically prepares such data for training and updating models.

In various embodiments, individual's pharmacy selection artificial intelligence model 108 is trained using a supervised or unsupervised machine learning program or algorithm. The machine learning program or algorithm may employ a neural network, which may be a convolutional neural network, a deep learning neural network, or a combined learning module or program that learns in two or more features or feature datasets in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. Machine learning may involve identifying and recognizing patterns in existing data (such as datasets described herein, including data of an individual's previous pharmacy selections, other data about the individual, and so forth) in order to facilitate making predictions for subsequent data (e.g., to select a preferred pharmacy for the patient).

In some embodiments, data sets (e.g., of the individual's past pharmacy selections, and other data) are used to train an ensemble of models with different architectures and/or hyperparameters. These different architectures could be K-nearest neighbors (KNN), support vector machines (SVM), deep neural nets (DNN), various decision trees, random forests, XGboost, or recurrent neural nets (RNN), to name just a few. In some embodiments, the results from the ensemble of models is then combined/rectified to produce a single predicted output, which is better than each of the individual models. These combination/rectification methods could be, for example, a majority vote, or it could estimate each of the models errors on a given data segment and then use these errors to produce a weighted mean, or it could rectify the different aggregation levels to produce a single prediction at the patient/medication level.

Machine learning model(s), such as individual's pharmacy selection artificial intelligence model 108, may be created and trained based upon example (e.g., "training data,") inputs or data (which may be termed "features" and "labels"), as described herein, in order to make valid and reliable predictions for new inputs, such as testing level or production level data or inputs. Examples of feature data that may be used to train individual's pharmacy selection artificial intelligence model 108 includes many of the above-discussed factors. For example, the model 108 may learn that an individual prefers to always find the pharmacy with the lowest price, and is willing to travel to a more distant pharmacy in order to fill the prescription at the pharmacy with the lowest price. On the other hand, the model 108 might indicate that another individual more often wants to minimize wait time or travel time.

In other examples, the model 108 might indicate that the individual has a strong preference for pharmacies where lockers are available, or where groceries are available. The model 108 can also include other data about the individual. For example, the model can include home and work addresses of the individual, and include this information when selecting a preferred pharmacy; this information is particularly relevant in examples where the model 108 also learns that the individual places a high priority on minimizing a travel time to the pharmacy. Furthermore, the model 108 can learn various commute routes of the individual (e.g., from GPS data, user input data, and so forth).

In still other examples, the model 108 might learn that the individual prefers to pickup the medication within a certain amount of time (e.g., the individual may receive the medication within 2 hours, 6 hours, 24 hours, or so forth).

In other examples, the AI model 108 keeps track of (or estimates) an amount of doses of a medication that the individual has remaining. For instance, the AI model 108 may know that the individual had previously picked up a 30 day supply of a medication, and has 5 days worth of medication left if the individual had been taking the medication at the prescribed rate. In this regard, when the system selects a preferred pharmacy or pharmacies, the system knows how urgent it is for the individual to receive the medication. In other examples, the AI model 108 learns that the individual prefers to pick up a medication on a certain day of the week.

In supervised machine learning, a machine learning program operating on a server, computing device, or other processor(s), may be provided with example inputs (e.g., "features") and their associated, or observed, outputs (e.g., "labels") in order for the machine learning program or algorithm to determine or discover rules, relationships, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Figure 6:
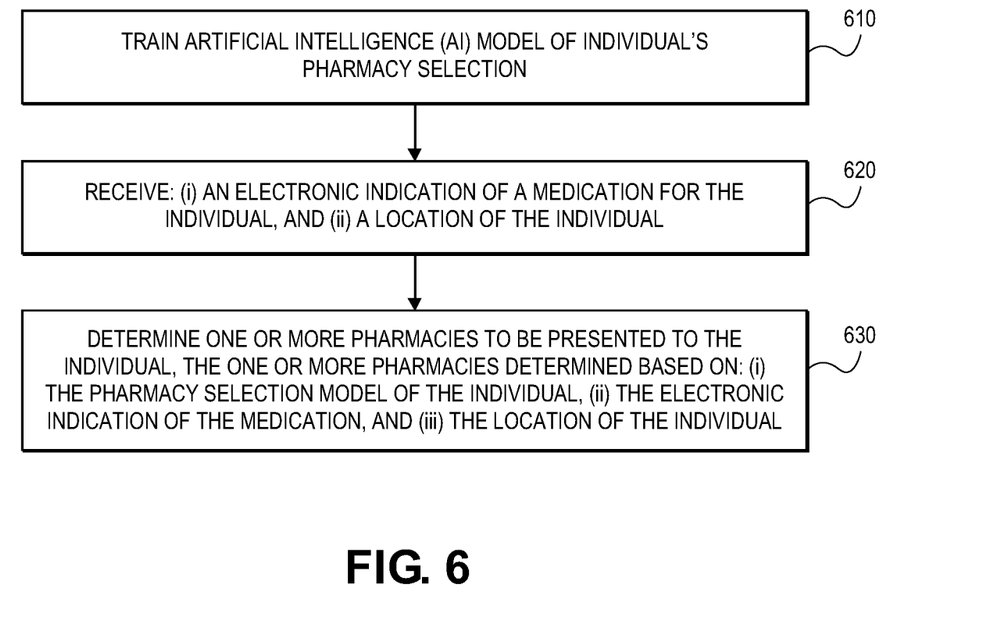
FIG. 6 shows an exemplary overview flowchart of an example embodiment using AI to train a model.

FIG. 6 illustrates an exemplary overview flowchart of an example embodiment involving using AI to train a model. With reference thereto, in step 610 an AI model of an individual's pharmacy selection is trained. At step 620, the system receives: (i) an electronic indication of a medication for the individual, and (ii) a location of the individual. At step 630, the system determines one or more pharmacies to be presented to the individual based on: (i) the pharmacy selection model of the individual, (ii) the electronic indication of the medication, and (iii) the location of the individual.

Figure 7:
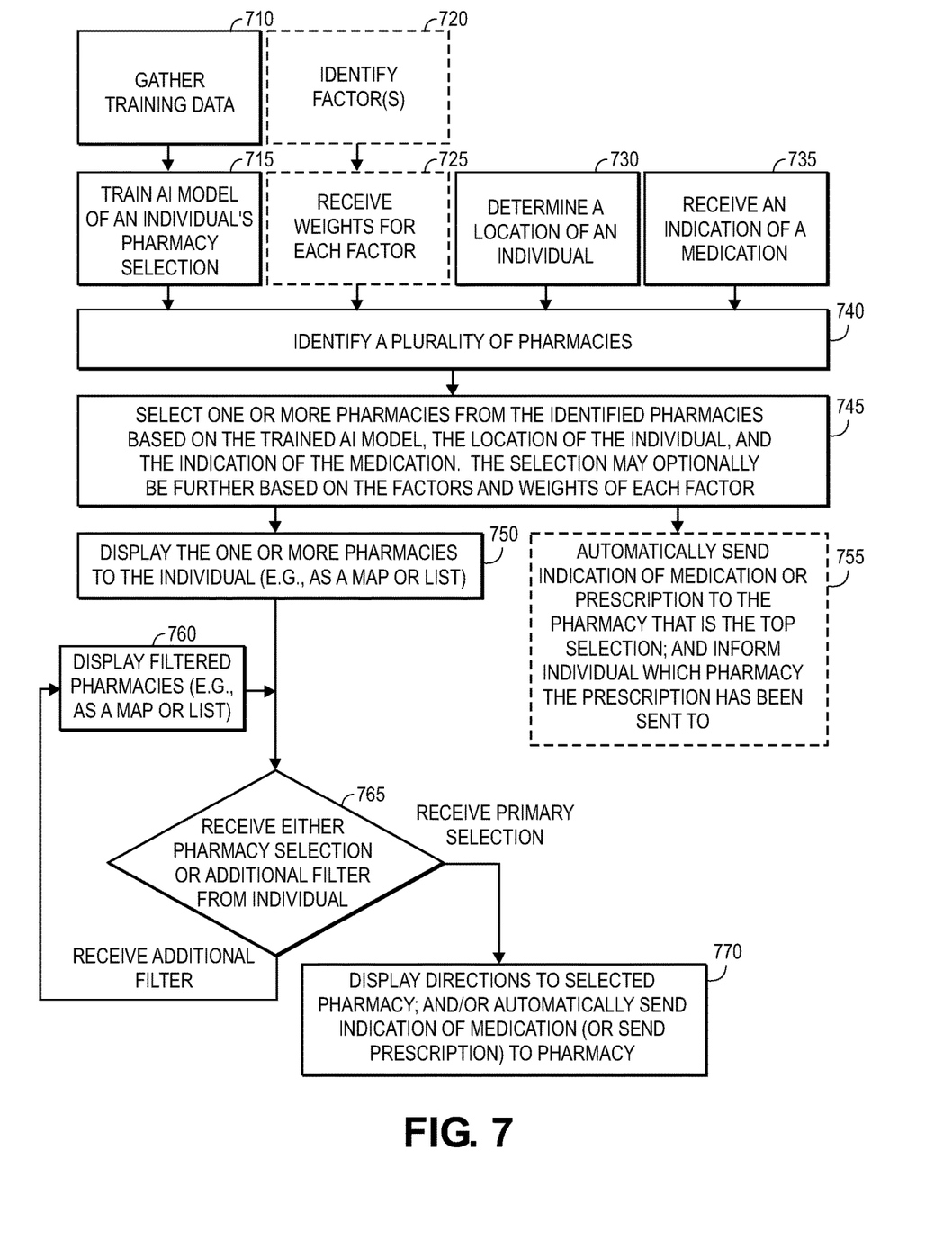
FIG. 7 illustrates a flowchart of another example embodiment.

FIG. 7 illustrates a flowchart of another example embodiment. With reference thereto, training data is gathered in step 710, and an AI model of an individual's pharmacy selection is trained in step 715. In an optional step 720, the individual may identify the factor(s) that the individual would like used in the section of the pharmacy. Again optionally, in step 725, the individual may assign weights to the factor(s). In step 730, the system determines a location of the individual. In step 735, the system receives an indication of a medication.

In step 740, the system identifies a plurality of pharmacies (e.g., all pharmacies within a particular geographic distance of the individual's location). In step 745, the system selects one or more pharmacies from the identified pharmacies. It should be understood that, in some embodiments, the identification step 740 and the selection step 745 may be combined into a single step. Further regarding selection step 745, the selection may be based on the trained AI model, the location of the individual, and the indication of the medication. The selection may optionally be further based on the factors and weights of each factor. Put another way, in some embodiments, the individual identifies factors (e.g., using smartphone 111*m*) (and also possibly assigns weights to the factors), and the pharmacy selection is done based on a combination of the identified factors and the AI model. In other embodiments, where the individual does not identify factors, the selection may be done based on the AI model without using any identification of factors from the individual.

In some embodiments, following the pharmacy selection, at optional step 755, the system automatically sends the indication of the medication (or prescription) to the pharmacy that is the top selection, and informs the individual which pharmacy the prescription has been sent to.

In some embodiments, at step 750, the system displays the one or more pharmacies to the individual (e.g., as a map or list). In some embodiments, subsequent to viewing the map or list, the individual selects a single pharmacy from the displayed one or more pharmacies; alternatively, the individual may apply a filter(s) (e.g., as previously described above) to the displayed one or more pharmacies (see, e.g., step 765). If additional filters are received, the system displays the filtered pharmacy or pharmacies (e.g., as a map or list) at step 760. If the individual makes a final selection of a pharmacy, the system may display directions to the pharmacy and/or automatically send the indication of the medication (or send the prescription) to the pharmacy at step 770.

Exemplary Embodiments Regarding Merchandise Pickup Location Selection

Although much of the foregoing discussion has been written to describe selection of a pharmacy, one having ordinary skill in the art will appreciate that the forgoing discussion also applies to selection of a merchandise pickup location. Particularly, the foregoing discussion applies to pickup of any item requiring a preparation time (e.g., a meal kit, beauty box, etc.). In this regard, examples of pickup locations include lockers, retail stores, drive-through pickups, curb-side pickups, drone pickup location (e.g., a location where drones deliver and/or receive items), and so forth.

In selecting a pickup location, a number of factors may be considered. For example, some factors that some embodiments consider are:

Whether the pickup location has the merchandise item in stock;

Preparation time for the merchandise item at the pickup location (e.g., preparation time for a meal kit;

Wait time at the pickup location;
Geographic distance to the individual;
Travel time to the pickup location including traffic and other travel factors;
Urgency of obtaining the merchandise item;
Price of the merchandise item(s);
Which product or class of products are available at the pickup location;
Whether a locker is available at the pickup location; and
Options for brand or item substitution (e.g., substituting brand A with brand B in a beauty box; substituting canola oil with corn oil in a meal kit; etc.), and how the substitutions effect: (i) price, (ii) pickup time, and/or (iii) nutrition.

Figure 8:
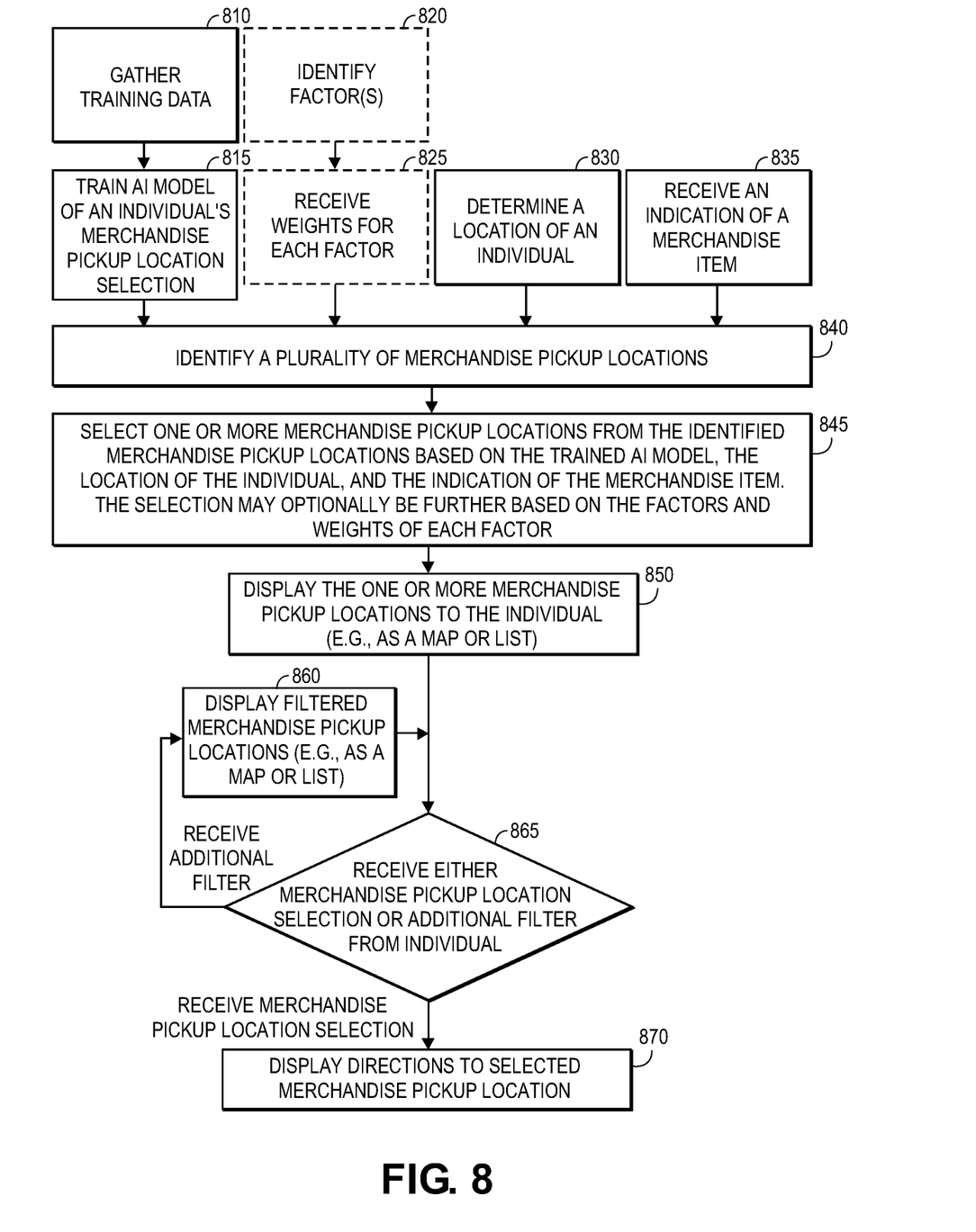
FIG. 8 illustrates a flowchart of an example embodiment of selecting a merchandise pickup location.

FIG. 8 illustrates a flowchart of example embodiment of selection of a merchandise pickup location. With reference thereto, training data is gathered in step 810, and an AI model of an individual's merchandise pickup location selection is trained in step 815. In an optional step 820, the individual may identify the factor(s) that the individual would like used in the section of the merchandise pickup location. Again optionally, in step 825, the individual may assign weights to the factor(s). In step 830, the system determines a location of the individual. In step 835, the system receives an indication of a merchandise item.

In step 840, the system identifies a plurality of merchandise pickup locations (e.g., all merchandise pickup locations within a particular geographic distance of the individual's location). In step 845, the system selects one or more merchandise pickup locations from the identified merchandise pickup locations. It should be understood that, in some embodiments, the identification step 840 and the selection step 845 may be combined into a single step. Further regarding selection step 845, the selection may be based on the trained AI model, the location of the individual, and the indication of the merchandise item. The selection may optionally be further based on the factors and weights of each factor. Put another way, in some embodiments, the individual identifies factors (e.g., using smartphone 111m) (and also possibly assigns weights to the factors), and the merchandise pickup location selection is done based on a combination of the identified factors and the AI model. In other embodiments, where the individual does not identify factors, the selection may be done based on the AI model without using any identification of factors from the individual.

In some embodiments, at step 850, the system displays the one or more merchandise pickup locations to the individual (e.g., as a map or list). In some embodiments, subsequent to viewing the map or list, the individual selects a single merchandise pickup location from the displayed one or more merchandise pickup locations; alternatively, the individual may apply a filter(s) (e.g., as previously described above) to the displayed one or more merchandise pickup locations (see, e.g., step 865). If additional filters are received, the system displays the filtered merchandise pickup location(s) (e.g., as a map or list) at step 860. If the individual makes a final selection of a merchandise pickup location, the system may display directions to the merchandise pickup location at step 870.

Additional Exemplary Embodiments

Aspect 1. In one aspect, there is a computer system for selecting a pharmacy, the computer system comprising one or more processors configured to:

using a machine learning algorithm and an initial training dataset, build a pharmacy selection model of an individual, wherein the initial data training dataset comprises data regarding: (i) which pharmacy or pharmacies the individual has previously used; (ii) travel times to the previously used pharmacies; (iii) wait times at previously used pharmacies; (iv) prices of medications the individual has purchased at the previously used pharmacies; (v) whether another product or class of products was available at the previously used pharmacies; and/or (vi) whether a locker was available at the previously used pharmacies;

receive: (i) an electronic indication of a medication for the individual, and (ii) a location of the individual; and determine one or more pharmacies to be presented to the individual, the one or more pharmacies determined based on: (i) the pharmacy selection model of the individual, (ii) the electronic indication of the medication, and (iii) the location of the individual.

Aspect 2. The computer system of aspect 1, wherein the one or more processors are further configured to:

using the machine learning algorithm, continuously update the pharmacy selection model of the individual based on subsequent pharmacy use by the individual.

Aspect 3. The computer system of aspect 1, wherein the one or more processors are configured to display, on a display, a map showing pharmacies of the determined plurality of pharmacies with:

pharmacies with a short fill time displayed as green;
pharmacies with an intermediate fill time displayed as yellow; and
pharmacies with a long fill time displayed as red.

Aspect 4. The computer system of aspect 1, wherein the one or more processors are further configured to:

display the determined plurality of pharmacies as a list in an order according to: (i) a prescription fill time, and (ii) a travel time from the location of the individual.

Aspect 5. A computer system for selecting a pharmacy, the computer system comprising one or more processors configured to:

receive, from an individual, an indication of a medication;
determine a location of the individual;
identify a plurality of pharmacies based on a first factor; and
select a preferred pharmacy from the plurality of pharmacies based on a second factor.

Aspect 6. The computer system of aspect 5, wherein the one or more processors are further configured to:

use a machine learning algorithm to create a pharmacy selection model corresponding to the individual; and
use the pharmacy selection model to determine the first and second factors.

Aspect 7. The computer system of aspect 5, wherein the one or more processors are further configured to determine the first and second factors from a plurality of factors including:

whether the pharmacy has a medication in stock;
wait time at the pharmacy;
geographic distance to the individual;
travel time from the location of the individual;
urgency of filling a prescription;
price of a prescription;
whether another product or class of products available at the pharmacy; and
whether a locker is available at the pharmacy.

Aspect 8. The computer system of aspect 5, wherein the first factor is geographic distance from the location of the individual.

Aspect 9. The computer system of aspect 5, wherein the one or more processors are further configured to:
determine the first factor and the second factor from a list of factors specified by the individual.

Aspect 10. The computer system of aspect 5, wherein the second factor is a travel time including road traffic.

Aspect 11. The computer system of aspect 5, wherein the second factor is a price of the indicated medication based on an insurance carrier of the individual.

Aspect 12. The computer system of aspect 5, wherein:
the second factor is an urgency of filling a prescription; and
the one or more processors are further configured to receive an input from the individual of an indication of the urgency as a time period.

Aspect 13. The computer system of aspect 5, wherein the second factor is whether groceries are available at the pharmacy.

Aspect 14. The computer system of aspect 5, wherein:
the preferred pharmacy is a first preferred pharmacy; and
and the one or more processors are further configured to:
select a second preferred pharmacy from the plurality of pharmacies based on the second factor; and
display the first and second preferred pharmacies to allow the individual to select between the first and second preferred pharmacies.

Aspect 15. The computer system of aspect 5, wherein the one or more processors are further configured to:
assign scores to each pharmacy of the plurality of pharmacies;
display the plurality of pharmacies on a map; and
color code each displayed pharmacy according to the assigned scores.

Aspect 16. The computer system of aspect 5, wherein the one or more processors are further configured to:
assign scores to each pharmacy of the plurality of pharmacies; and
display the plurality of pharmacies as a list in an order according to the assigned scores.

Aspect 17. The computer system of aspect 5, wherein the one or more processors are further configured to:
send a prescription corresponding to the indicated medication to the preferred pharmacy;
receive a locker assignment for storage of medication of the prescription; and
send the locker assignment to the individual.

Aspect 18. A computer system for selecting a pharmacy, the computer system comprising one or more processors configured to:
receive an indication of a medication;
determine a location of an individual;
identify a plurality of pharmacies;
determine: (i) a travel time from the location of the individual to each pharmacy of the plurality of pharmacies, and (ii) for each pharmacy of the plurality of pharmacies, a prescription fill time; and
select a preferred pharmacy from the plurality of pharmacies based on: (i) the determined travel time, and (ii) the determined prescription fill times.

Aspect 19. The computer system of aspect 18, wherein the one or more processors are further configured to:
use a machine learning algorithm to create a pharmacy selection model corresponding to the individual; and
select the preferred pharmacy further based on the pharmacy selection model corresponding to the individual.

Aspect 20. The computer system of aspect 18, wherein the one or more processors are further configured to:
receive, from the individual, an indication of importance between travel time and prescription fill time; and
select the preferred pharmacy further based on the indication of importance.

Aspect 21. The computer system of aspect 18, wherein the one or more processors are configured to display, on a display, a map showing pharmacies of the plurality of pharmacies with:
pharmacies with a short fill time displayed as green;
pharmacies with an intermediate fill time displayed as yellow; and
pharmacies with a long fill time displayed as red.

Aspect 22. The computer system of aspect 18, wherein the determination of prescription fill time for each pharmacy of the plurality of pharmacies are based on inventory data of each pharmacy of the plurality of pharmacies.

Aspect 23. The computer system of aspect 18, wherein the one or more processors are further configured to determine the travel times based on road traffic data.

Aspect 24. The computer system of aspect 18, wherein the one or more processors are further configured to send, to the preferred pharmacy, a prescription corresponding to the indication of the medication.

Other Matters

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of geographic locations.

What is claimed:

1. A computer system for selecting a pharmacy, the computer system comprising one or more processors configured to:
using a machine learning algorithm and an initial training dataset, build a pharmacy selection model of an individual, wherein the initial data training dataset comprises data regarding: (i) which pharmacy or pharmacies the individual has previously used; (ii) travel times to the previously used pharmacies; (iii) wait times at the previously used pharmacies; (iv) prices of medications the individual has purchased at the previously used pharmacies; (v) whether another product or class of products was available at the previously used pharmacies; and/or (vi) whether a locker was available at the previously used pharmacies, the machine learning algorithm trained by producing a predicted output based on a weighted average from a plurality of artificial intelligence model error estimates;
receive: (i) an electronic indication of a medication for the individual, and (ii) a location of the individual; and
determine one or more pharmacies to be presented to the individual, the one or more pharmacies determined based on: (i) the pharmacy selection model of the individual, (ii) the electronic indication of the medication, and (iii) the location of the individual.

2. The computer system of claim 1, wherein the one or more processors are further configured to:
using the machine learning algorithm, continuously update the pharmacy selection model of the individual based on subsequent pharmacy use by the individual.

3. The computer system of claim 1, wherein the one or more processors are configured to display, on a display, a map showing pharmacies of the determined plurality of pharmacies with:
pharmacies with a short fill time displayed as green;
pharmacies with an intermediate fill time displayed as yellow; and
pharmacies with a long fill time displayed as red.

4. The computer system of claim 1, wherein the one or more processors are further configured to:
display the determined plurality of pharmacies as a list in an order according to: (i) a prescription fill time, and (ii) a travel time from the location of the individual.

5. A computer system for selecting a pharmacy, the computer system comprising one or more processors configured to:
receive, from an individual, an indication of a medication;
determine a location of the individual;
use a machine learning algorithm to create a pharmacy selection model corresponding to the individual, the machine learning algorithm trained by producing a predicted output based on a weighted average from a plurality of artificial intelligence model error estimates; and
use the pharmacy selection model to determine first and second factors;
identify a plurality of pharmacies based on a first factor; and
select a preferred pharmacy from the plurality of pharmacies based on a second factor.

6. The computer system of claim 5, wherein the one or more processors are further configured to determine the first and second factors from a plurality of factors including:
whether the pharmacy has a medication in stock;
wait time at the pharmacy;
geographic distance to the individual;
travel time from the location of the individual;
urgency of filling a prescription;
price of a prescription;
whether another product or class of products available at the pharmacy; and
whether a locker is available at the pharmacy.

7. The computer system of claim 5, wherein the first factor is geographic distance from the location of the individual.

8. The computer system of claim 5, wherein the second factor is a travel time including road traffic.

9. The computer system of claim 5, wherein the second factor is a price of the indicated medication based on an insurance carrier of the individual.

10. The computer system of claim 5, wherein:
the second factor is an urgency of filling a prescription; and
the one or more processors are further configured to receive an input from the individual of an indication of the urgency as a time period.

11. The computer system of claim 5, wherein the second factor is whether groceries are available at the pharmacy.

12. The computer system of claim 5, wherein:
the preferred pharmacy is a first preferred pharmacy; and
the one or more processors are further configured to:
select a second preferred pharmacy from the plurality of pharmacies based on the second factor; and
display the first and second preferred pharmacies to allow the individual to select between the first and second preferred pharmacies.

13. The computer system of claim 5, wherein the one or more processors are further configured to:
assign scores to each pharmacy of the plurality of pharmacies;
display the plurality of pharmacies on a map; and
color code each displayed pharmacy according to the assigned scores.

14. The computer system of claim 5, wherein the one or more processors are further configured to:
assign scores to each pharmacy of the plurality of pharmacies; and
display the plurality of pharmacies as a list in an order according to the assigned scores.

15. The computer system of claim 5, wherein the one or more processors are further configured to:
send a prescription corresponding to the indicated medication to the preferred pharmacy;
receive a locker assignment for storage of medication of the prescription; and
send the locker assignment to the individual.

16. A computer system for selecting a pharmacy, the computer system comprising one or more processors configured to:
use a machine learning algorithm to create a pharmacy selection model corresponding to an individual, the machine learning algorithm trained by producing a predicted output based on a weighted average from a plurality of artificial intelligence model error estimates;
receive an indication of a medication;
determine a location of the individual;
identify a plurality of pharmacies;
determine: (i) a travel time from the location of the individual to each pharmacy of the plurality of pharmacies, and (ii) for each pharmacy of the plurality of pharmacies, a prescription fill time; and
select a preferred pharmacy from the plurality of pharmacies based on: (i) the determined travel time, (ii) the determined prescription fill times, and (iii) the pharmacy selection model corresponding to the individual.

17. The computer system of claim 16, wherein the one or more processors are further configured to:
receive, from the individual, an indication of importance between travel time and prescription fill time; and
select the preferred pharmacy further based on the indication of importance.

18. The computer system of claim 16, wherein the one or more processors are configured to display, on a display, a map showing pharmacies of the plurality of pharmacies with:
pharmacies with a short fill time displayed as green;
pharmacies with an intermediate fill time displayed as yellow; and
pharmacies with a long fill time displayed as red.

19. The computer system of claim 16, wherein the determination of prescription fill time for each pharmacy of the plurality of pharmacies are based on inventory data of each pharmacy of the plurality of pharmacies.

20. The computer system of claim 16, wherein the one or more processors are further configured to determine the travel times based on road traffic data.

21. The computer system of claim 16, wherein the one or more processors are further configured to send, to the preferred pharmacy, a prescription corresponding to the indication of the medication.

22. The computer system of claim 1, wherein the initial data training dataset comprises the data regarding (iii) wait times at the previously used pharmacies.

23. The computer system of claim 1, wherein the initial data training dataset comprises the data regarding (vi) whether the locker was available at the previously used pharmacies.

\* \* \* \* \*